United States Patent [19]

Gatzi

[11] 3,932,509
[45] Jan. 13, 1976

[54] CARBAMOYLOXIMES DERIVATIVES

[75] Inventor: Karl Gatzi, Basel, Switzerland

[73] Assignee: Ciba-Geigy Corporation, Ardsley, N.Y.

[22] Filed: June 26, 1974

[21] Appl. No.: 483,203

Related U.S. Application Data

[62] Division of Ser. No. 124,527, March 15, 1971, Pat. No. 3,843,724.

[30] Foreign Application Priority Data

Mar. 23, 1970 Switzerland.......................... 4319/70

[52] U.S. Cl.......................................... 260/566 AC
[51] Int. Cl.².................................... C07C 131/02
[58] Field of Search ............................. 260/566 AC

[56] References Cited
UNITED STATES PATENTS 3,063,823  11/1962  Kuhle et al............... 260/566 AC X
3,705,195  12/1972  Weis et al. .................... 260/566 AC
3,843,724  10/1974  Gatzi............................ 260/566 AC

OTHER PUBLICATIONS

Weiden, J. Sci. Fd. Agric. Suppl., pp. 19–30 (1968).

*Primary Examiner*—Gerald A. Schwartz
*Attorney, Agent, or Firm*—Harry Falber

[57] ABSTRACT

Carbamoyl oximes of the formula

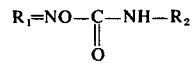

their manufacture and fungicidal and virucidal activity are disclosed. In this formula $R_1$ stand for alkylidene, aralkylidene or mono-, bi- or tricycloalkylidene and $R_2$ stands for $C_8$ to $C_{14}$ alkyl, mono- or bicycloalkyl or cycloalkenyl.

6 Claims, No Drawings

CARBAMOYLOXIMES DERIVATIVES

This is a division of application Ser. No. 124,527, filed on Mar. 15, 1971, now U.S. Pat. No. 3,843,724.

The present invention relates to new carbamoyloximes, to processes for their production, also to agents which contain these carbamoyloximes as active substances and which are used for the control of phytopathogenic fungi and viruses, and to methods for the controlling of phytopathogenic fungi and viruses using the new active substances or agents containing them. The new carbamoyloximes correspond to formula I:

$$R_1=NO-\underset{\underset{O}{\|}}{C}-NHR_2 \qquad (I)$$

wherein
- $R_1$ represents an alkylidene radical optionally substituted by alkoxy, an aralkylidene radical, an optionally lower-alkyl-substituted cycloalkylidene, bicycloalkylidene, or tricycloalkylidene radical,
- $R_2$ represents an alkyl radical having 8 to 14 carbon atoms, an optionally lower-alkyl-substituted cyloalkyl, cycloalkenyl, or bicycloalkyl radical.

In formula I, $R_1$ stands for hydrocarbon radicals having a bivalent carbon atom. In the case of alkylidene radicals, this bivalent C-atom is always the intermediate member; in the case of aralkylidene radicals, it can be either the intermediate member or the end member of the aliphatic chain. Alkylidene radicals are branched or straight-chain, and have 3 to 9 carbon atoms in the chain. Such an alkylidene radical can be substituted by one or several lower alkoxy radicals containing 1 to 4 carbon atoms, such as, e.g. methoxy, ethoxy, propoxy and isopropoxy. The aliphatic part of an aralkylidene radical has 1 to 5 carbon atoms; and phenyl or phenyl substituted by halogen or low alkyl such as e.g. chlorine, bromine and/or methyl constitutes the aryl part. Cycloalkylidene radicals $R_1$ contains 5 to 12 carbon atoms as ring members, can carry alkyl radicals as substituents, especially low alkyl containing 1 to 4 carbon atoms, e.g. methyl and/or isopropyl radicals. As cycloalkylidene radicals, radicals of cyclopentane, cyclohexane and cyclododecane are preferred. With respect to the bicycloalkylidene radicals, these are, in particular, radicals of bicyclic terpenes; and by tricycloalkylidene radicals is meant especially a tricycloheptylidene radical. By an alkyl radical $R_2$ having 8 to 14 carbon atoms is meant, in particular, a straight-chain radical such as, e.g. the n-octyl, n-decyl, n-dodecyl and n-tetradecyl radical. Mentioned as cycloalkyl and cycloalkenyl radicals are particularly the cyclohexyl and cyclohexenyl radicals, which can carry as substituents lower alkyl radicals containing 1 to 4 carbon atoms, preferably methyl and/or isopropyl radicals. A bicycloalkyl radical $R_2$ is preferably a bicycloheptyl radical, e.g. the bicyclo [4.1.0]heptyl radical, or a radical of a bicyclic terpene, such as a radical of bornane, of norbornane or of 1,3,3,-trimethylbornane.

The new carbamoyloximes of formula I are produced according to the present invention by reacting an oxime of formula II:

$$R_1 = NOH \quad (II)$$

a. with an isocyanate of formula III:
$$R_2NCO \quad (III)$$
optionally in the presence of a catalyst, or
b. with a carbamic acid halide of formula IV:

$$Hal - CO - NHR_2 \quad (IV)$$

in the presence of an acid-binding agent, or c. with the formation components of a carbamic acid halide, namely, phosgene and an amine of formula V:
$$NH_2R_2 \quad (V)$$
in the presence of an acid-binding agent.

In formulae II to V, the symbols $R_1$ and $R_2$ have the meanings given under formula I; in formula IV, Hal stands for chlorine or bromine.

Instead of an isocyanate of formula III or a carbamic acid halide of formula IV, it is possible to use for the process according to the invention also the mixture of an isocyanate of formula III and the corresponding carbamic acid halide of formula IV.

The reactions according to the invention are performed in the presence of acid-binding agents, such as inorganic bases, e.g. hydrides, hydroxides and carbonates of alkali metals and alkaline-earth metals; or organic nitrogen bases, e.g. tertiary amines such as pyridine, triethylamine, dimethylaniline, etc. Furthermore, as catalysts for the reaction with the isocyanates of formula III are used, e.g. tertiary amines or organotin compounds. It is preferable to perform the reactions in solvents or diluents inert to the reactants, e.g. in ethers or ethereal compounds such as diethylether, dipropylether, dioxane, tetrahydrofuran; in amides such as N,N-dialkylated carboxylic acid amides; as well as in halogenated hydrocarbons, or aliphatic or aromatic hydrocarbons.

The new carbamoyloximes are obtained using the process according to the invention in good to very good yields. They are soluble and stable in the usual organic solvents.

It is known that oximes can exist in two stereoisomeric forms: the syn- and anti-form. The carbamoyloximes of formula I too exist in these two forms. Accordingly, the term "carbamoyloximes of formula I" in the case of the present invention covers both stereoisomeric forms.

The starting materials of formula II used for the reactions according to the invention are known compounds and can be produced by known methods.

The new carbamoyloximes of formula I have an excellent fungicidal and viricidal action on numerous phytophatogenic fungi and viruses respectively. As phytopathogenic fungi, e.g. mildew fungi such as the powdery mildew of cucumbers (*Erysiphe cichoracearum*), powdery mildew of apples (*Podosphaera leucotricha*), powdery mildew of roses (*Sphaerotheca pannosa*), powdery mildew of wheat (*Erysiphe graminis*); as well as downy mildew fungi, such as the one causing the blight on leaves and tubers of potatoes (*Phytophthora infestans*); downy mildew of vines (*Plasmophora viticola*); also leaf spot fungi such as those causing the grey speck disease of tomatoes (*Alternaria solani*), leaf spot of celery (*Septoria spicola*); and rust fungi such as bean rust (*Uromyces appendiculatus*); also grey mould (*Botrytis cinera*) which is very difficult to control, etc. may be mentioned. As phytopathogenic viruses the following may for example be mentioned; bacilliform viruses as for example the tobacco mosaic virus or the potato-M-virus, filiform viruses as for example the potato-Y-virus or the carrot yellowing virus and spheroidal viruses as for example the cucumber mosaik virus. In addition to a persistent action, the compounds also have a good curative effect, so that even fungi and viruses which have already pentrated into the plant tissue are killed off by application of the new compounds.

Moreover, various carbamoyloximes of formula I also possess insecticidal and acaricidal properties. Since the compounds are not phytotoxic and have a favourable toxicity with regard to warm-blooded animals, they are most suitable for the protection of plants.

Preferred compounds of the invention are carbamoyloximes having the formula VI

wherein $R_3$ represents a mono or bicyclic alkylidene radical containing 5 to 7 carbon atoms optionally substituted by a low alkyl group, a straight chained alkyl group containing 3 to 9 carbon atoms optionally substituted by a low alkoxy group or a phenyl-low-alkylidene radical optionally halogen-substituted and $R_4$ represents a cycloalkenyl-mono- or bicyclicalkyl- radical with 5 to 7 carbon atoms optionally substituted by a low alkyl group or a straight chained alkyl group containing 8 to 12 carbon atoms whereby low alkyl, low alkoxy and halogen have the meanings given above.

In the group of compounds having the formula VI the compounds of the formula VII

are especially noteworthy.

In formula VII $R_5$ represents a cyclopentylidene, cyclohexylidene, cycloheptylidene, 1,4-menthylidene(3), bornylidene, norbornylidene, 5-nonylidene, butylidene, 1,1-dimethoxybutylidene, benzylidene, p-chlorobenzylidene, phenyl-1-ethylidene or phenyl-1-propylidene group and represents a dodecyl, cyclohexyl, 1,4-menthyl(3), 3,5,5-trimethylcy-clohexen(2)-yl, bornyl or 1,3,3-trimethylnorbornyl group.

Fungicidal and viricidal agents according to the invention are produced in a manner known per se by the intimate mixing and grinding of active substances of the general formula I with suitable carriers, optionally with the addition of dispersing agents or solvents which are inert to the active substances. The active substances can be used for the production of dusting agents, scattering agents, granulates, coated granulates, impregnated granulates, homogeneous granulates, wettable powders, pastes, emulsions, solutions, or aerosols.

Solid preparations (dusting agents, scattering agents, granulates) are produced by mixing together the active substances with solid carriers. The particle size of the carriers for dusting agents is advantageously up to ca. 0.1 mm, for scattering agents ca. 0.075 to 0.2 mm, and for granulates 0.2 mm or more. The concentration of active substances in the solid preparations is, as a rule 0.01- 95 preferably 0.5 to 80 %. To these mixtures may also be added additives stabilising the active substance, and/or non-ionic, anion-active, and cation-active substances which, for example, improve the adhesiveness of the active substances on plants and parts of plants (adhesives and agglutinants), and/or ensure a higher degree of wettability (wetting agents) and also of dispersibility (dispersing agents). The amounts in which these agents are employed are chosen such that the applied quantity of active substance is between 0.5 10 kg/hectare.

Water-dispersible active substance concentrates, wettable powders, pastes and emulsion concentrates constitute agents which can be diluted with water to obtain any desired concentration. They consist of active substance, carrier, surface-active substances, and anti-foaming agents and, optionally solvents. The active substance concentration in these agents is 5–80%. The wettable powders and the pastes are obtained by mixing and grinding the active substances with dispersing agents and pulverulent carriers, in suitable devices, until homogeneity is obtained. It is advantageous in some cases to use mixtures of different carriers. Suitable anti-foaming agents are, e.g. silicones. The active substances are mixed, ground, sieved and filtered with the above mentioned additives in such a manner that in the case of the wettable powders the solid part does not exceed a particle size of 0.02 to 0.04 mm., and in the case of the pastes a particle size of 0.003 mm. Used for the production of emulsion concentrates and pastes are dispersing agents, organic solvents, and water. The solvents must be practically without smell; they must also be inert to the active substances, not phytotoxic, and not readily combustible.

Furthermore, the agents according to the invention can be used in the form of solutions. For this purpose the active substance or several active substances of the general formula I is or are dissolved in suitable organic solvents, mixtures of solvents, or water. The solutions are to contain the active substances in a concentration range of 1 – 20%. To the described agents according to the invention can be added other biocidal active substances or agents. The new agents can thus contain, in addition to the stated compounds of the general formula I, and other fungicides, e.g. insecticides, herbicides, bactericides, fungistatica, bacteriostatica, or nematocides, for the purpose of widening the range of action of the new agents. The agents according to the invention may also contain fertilisers, trace elements etc. As active substances which may be mixed with the compounds of the invention the following may be mentioned amongs others:

Inorganic substances

Elemental sulphur, ammonium polysulphide, sodium polysulphide, barium polysulphide, calcium polysulphide and calcium thiosulphate (lime sulphur), calcium hypochlorite, boric acid, sodium tetraborate-decahydrate (borax), zinc chloride, magnesium borate, nickel sulphate, potassium chromate, lead arsenate, cadmium chloride, and cadmium carbonate;

Copper substances

Copper (I) oxide (cuprous oxide), Bordeaux mixture, copper (II) sulphate-pentahydrate (copper sulphate), basic copper (II) chloride (copper oxychloride), copper(II) phosphate, tribasic copper (II) sulphate (tribasic copper sulphate), basic copper (II) carbonate, copper (II) dihydrazine sulphate, a copper-amine complex, copper (II) sulphate/ammonium carbonate mixture, copper(II) chloride/basic copper(II) sulphate mixture, basic copper(II) carbonate/zinc salt mixture, copper- (II)-zinc chromate complex (copper zinc chromate), copper(II)-zinc-cadmium-calcium chromate complex, copper(II) salt of oleic acid (copper oleate), a copper-(II) salt of a fatty acid, copper(II) salt of naphthenic acid (copper naphthenate), copper (II) salt of 8-hydroxyquinoline (oxine copper), copper(II) salt of 1,2-naphthoquinoncoxime-(2), and copper (II) salt of 1,2-naphthoquinoneoxime-(2), and copper (II) salt of 3-phenylsalicylate;

Tin and mercury substances

Bis-(tri-n-butyl tin)oxide, triphenyl tin hydroxide (fentin hydroxide), triphenyl tin acetate (fentin acetate), bis-(tributyl tin)succinate, mercury (I) chloride (calomel), mercury (II) chloride (mercuric chloride), mercury (II) oxide, mercury-zinc chromate complex, mercury (II) lactate, ethylmercury chloride, 2-hydroxyethyl mercury acetate, ethylmercury isothiocyanate, 3-ethoxypropyl mercury bromide, chloromethoxypropyl mercury acetate, methoxyethyl mercury chloride, 2-methoxyethyl mercury silicate, bis-(methylmercury) sulphate, bis-(methylmercury) ammonium acetate, ethylmercury acetate, 2-methoxyethylmercury acetate, ethylmercury phosphate, isopropylmethylmercury acetate, methylmercury cyanide, methylmercury benzoate, N-cyano-N'(methylmercury) guanidine, methylmercury pentachlorophenolate, ethylmercury-2,3-dihydroxypropyl mercaptide, methylmercury-8-hydroxyquinolate (Ortho LM), N-(methylmercury)-1,4,5,6,7,7-hexachlorobicyclo[2,2,1]hept-5-ene-2,3-dicarboximide, N-(ethylmercury)-1,4,5,6,7,7-hexachlorobicyclo[2,2,1]hept-5-ene-2,3-dicarboximide, sodium salt of ethylmercury thiosalicylate, N-(ethylmercury)-para-toluenesulphonic acid anilide, phenylmercury acetate (PAM), phenylmercury propionate, phenylmercury triethanolammonium lactate (PAS), phenylmercury urea, N-(phenylmercury)-1,4,5,6,7,7-hexachlorobicyclo[2,2,1]hept-5-ene-2,3-dicarboximide, phenylmercury dimethyldithiocarbamate, phenylmercury formamide, phenylmercury chloride, phenylmercury acetate, phenylmercury benzoate, phenylmercury borate, phenylmercury hydroxide, phenylmercury iodide, basic phenylmercury nitrate, phenylmercury monoethanolamine lactate, phenylmercury salicylate, hydroxymercury chlorophenol, hydroxymercury trichlorophenol, hydroxymercury nitrophenol, N-phenylmercury ethylenediamine, phenylmercury monoethanolammonium acetate, pyridylmercury acetate, diphenylmercury-8-hydroxyquinolate, a mercury (II) complex with an organic phosphate, mixture of methylmercury-2,3-dihydroxypropylmercaptide and methylmercury acetate, mixture of hydroxymercury chlorophenol and hydroxymercury nitrophenol, and mercury-cadmium organic complex;

Further organic metal compounds

Cadmium succinate, cadmium-di-n-propylxanthogenate, cadmium-8-hydroxyquinolate, phenylaminocadmium acetate, phenylaminocadmium dilactate, methylarsine sulphide, zinc octate and zinc oleate;

Simple organic compounds (aliphates)

Formalin, paraformaldehyde, acrolein, methyl bromide, methyl isothiocyanate, tetraiodoethylene, 1,3-dichloropropene and related chlorinated $C_3$ hydrocarbons, 1-chloro-3-bromopropene (1), trans-1,4-dibromobutene(2), 1,3-dichloropropene(1), 1-chloro-2-nitropropane, 2-chloro-1-nitropropane trichloronitromethane, dichlorotetrafluoro-acetone, sodium salt of propionic acid, calcium salt of propionic acid, chlorofumaric acid-bis-β-chloroethyl ester, sorbic acid and the potassium salt thereof, 2-propene-1,1-diolacetate, 2-aminobutane, dodecylguanidine acetate (dodine), dodecylguanidine phthalate, α-chloroacetyl-1,3-aminopropionitrile, α-bromoacetylvalinamide, 1,2-dichloro-1-(methylsulphonyl) ethylene, 1,2-dichloro-1-(butylsulphonyl)ethylene, and trans 1,2-bis-(n-propylsulphonyl)ethylene;

Benzene derivatives

Para-dichlorobenzene, hecta-chlorobenzene (HCB), 1,2,4,5-tetrachloro-4-nitrobenzene (tecnazene), pentachloronitrobenzene (quintozene), 1,3,5-trichloro-2,4,6-trinitrobenzene, isomer mixture of 1,3,4-trichloro-2,6-dinitrobenzene and 1,2,3-trichloro-4,6-dinitrobenzene, 2,4,5,6-tetrachloroisophthalic acid nitrile, 2,4-dinitrophenylthiocyanate, diphenyl, ortho-nitrodiphenyl, 1-chloro-2,4-dinitronaphthalene, acenaphthene;

Phenols 2,4,6-trichlorophenol, 2,4,5-trichlorophenol, 2,4,5-trichlorophenyl acetate, 2,4,5-trichlorophenyl chloroacetate, trichlorophenol zinc salt, meta-cresyl acetate, 2,3,4,6-tetrachlorophenol, pentachlorophenol (PCP), ortho-dihydroxybenzene, 2,4-dihydroxy-n-hexylbenzene, 2-phenylphenol (ortho-phenylphenol), 3,5-dibromosalicylic aldehyde, 2-benzyl-4-chlorophenol, 2,2'-dihydroxy-5,5'-dichlorodiphenylmethane (dichlorophene), 2,2'-dihydroxy-3,3',5,5',6,6'-hexachlorodiphenylmethane, 2,2'-dihydroxy-5,5'-dichlorophenylsulphide, 2,2'-dihydroxy-3,3',5,5'-tetrachlorodiphenylsulphide, 2,2'-dihydroxy-3,3',5,5'-tetrachlorodiphenylsulphide disodium salt, 4-chloro-orthophenylphenol, 1,4-dichloro-2,5-dimethoxybenzene, salicylic anilide, bismuthsalicylate, trifluoromethylsalicylic anilide halogenated with chlorine or bromine, brominated salicylic anilide, and (3,5-dimethyl-4-chlorophenoxy)-ethanol;

Dinitrophenol derivatives 2-(1-methyl-n-propyl)-4,6-dinitrophenyl-2-methylcrotonate (binapacryl), 2-(1-methyl-n-propyl)-4,6-dinitrophenylisopropylcarbonate (dinobuton), 2-(1-methyl-n-heptyl)-4,6-dinitrophenylcrotonate (dinocap), methyl-2,6-dinitro-4-(1-ethylhexyl)phenylcarbonate + methyl-2,6-dinitro-4-(1-propylphenyl)phenylcarbonate (dinocton p), 4-nonyl-2,6-dinitrophenylbutyrate, and S-methyl-2-(1-methyl-n-heptyl)-4,6-dinitrophenylthiocarbonate;

Aniline derivatives 2,6-dichloro-4-nitroaniline (dichloran), 2-cyanoethyl-N-phenylcarbamate, propynyl-N-phenylcarbamate, and α-(2-bromoacetoxy)-actanilide;

Quinone derivatives 2,3,5,6-tetrachlorobenzoquinone(1,4) (chloranil), 2,3-dichloronaphthoquinone(1,4) (dichlone), 2-amino-3-chloronaphthoquinone(1,4), 2,3,6,7-tetrachloro-4α,8α-epoxy-1,2,3,4,4a,8a-hexahydro-1,4-methanonaphthalene-5,8-dione, and quinonoximebenzoylhydrazone (benquinox);

Trichloromethylthio derivatives

N-(trichloromethylthio)phthalimide (folpet), N-(trichloromethylthio)cyclohex-4-ene-1,2-dicarboximide (captan), N-(1,1,2,2-tetrachloroethylthio)cyclohex-4-ene-1,2-dicarboximide (captafol), N-methanesulphonyl-N-trichloromethylthio-para-chloroaniline, N'-dichlorofluoromethylthio-NN-dimethyl-N'-phenylsulphamide (dichlofluanid), and S-(2-pyridyl-1-oxide)-S'-trichloromethyl disulphide; hydrochloride;

Organic Phosphates

O,O,O-trimethylthiophosphate, O,O-diethylphthalimidophosphonothioate, 5-amino-bis-(dimethylamido)phosphinyl-3-phenyl-1,2,4-triazolo (triamiphos), 5-methylamino-bis(dimethylamido)phosphinyl-3-phenyl-1,2,4-triazole, O,O-diethyl-O-2-pyrazinylphosphorthicate, O-ethyl-S,S-diphenyldithiolphosphate, O-ethyl-S-benzylphenyldithiophosphonate, and O,O-diethyl-S-benzylthiolphosphate;

Dithiocarbamates

Zinc salt of dithiocarbazine acid, sodium-N-methyldithiocarbamate (metham), sodium-N-methoxyethyldithiocarbamate, sodium-N,N-dimethyldithiocarbamate (DDC), ammonium-N,N-dimethyldithiocarbamate, zinc-N,N-dimethyldithiocarbamate (ziram), iron-N,N-dimethyldithiocarbamate (ferbam), copper-N,N-dimethyldithiocarbamate, disodium-ethylene-1,2-bis-dithiocarbamate (nabam), zinc-ethylene-1,2-bis-dithiocarbamate (zineb), iron-ethylene-1,2-bis-dithiocarbamate, manganese(II)-ethylene-1,2-bis-dithiocarbamate (maneb), calcium-ethylene-1,2-bis-dithiocarbamate, ammonium-ethylene-1,2-bis-dithiocarbamate, zinc-propylene-1,2-bis-dithiocarbamate (mezineb) (propineb), bis(dimethylthiocarbamyl) ethylene-1,2-bis-dithiocarbamate, complex consisting (maneb) and zinc salt (manozeb), tetra-ethylthiuram monosulphide, bis-(N,N-dimethyldithiocarbamylmercapto)-methylarsine, tetramethylthiuramdisulphide (thiram), dipyrrolidylthiuramdisulphide, N,N'-bis-(dimethylamino)thiuramdisulphide polyethylenethiuramsulphide, and complex consisting of (zineb) and polyethylenethiuramdisulphide (metiram);

O-Heterocycles

Bis-(3,4-dichloro-2(5)-furanoyl)ether (mucochloric anhydride 2-methoxymethyl-5-nitrofuran, 5-nitrofurfuraldoxime-(2), 5-nitorfurfurylamideoxime-(2), and 1-hydroxy-3-acetyl-6-methylcyclohexene-(5)-dione-(2,4) (dehydroacetic acid);

1-N-Heterocycles

3-[2-(3,5-dimethyl-2-hydroxycyclohexyl)-2-hydroxyethyl]-glutarimide (cycloheximide), phthalimide, pyridine-2-thiol-1-oxide or 1-hydroxypyridine-2-thione, zinc salt of pyridine-2-thiol-1-oxide, manganese(I) salt of pyridine-2-thiol-1- oxide, S-1(1-oxido-2-pyridyl)isothiuronium chloride $\alpha,\alpha$-bis(4-chlorophenyl)-3-pyridinemethanol (parinol), 8-hydroxyquinoline (8-quinolinol), 8-hydroxyquinoline sulphate (quinosol), benzoyl-8-hydroxyquinoline salicylate, 3-(2-methylpiperidino)propyl-3,4-dichlorobenzoate, 6-ethoxy-1,2-dihydro-2,2,4-trimethylquinoline (ethoxyquin), N-lauryl-isoquinolinium bromide, 9-(para-n-hexyloxyphenyl)-10-methylacridinium chloride, and 9-(para-n-hexyloxyphenyl)-10-methylacridinium-para-toluene sulphonate;

2- and 3-N-heterocycles 2-n-heptadecylimidazolidine acetate (glyodine), 1-hydroxyethyl-2-heptadecylimidazolidine, 1-phenyl-3,5-dimethyl-4-nitrosopyrazole, 1-para-chlorophenyl-3,5-dimethyl-4-nitorsopyrazole, 1-para-sulphamylphenyl-3,5-dimethyl-4-nitrosopyrazole, N-(1-phenyl-2-nitropropyl)piperazine, 2-dimethylamino-6-methyl-5-n-butyl-4-hydroxypyrimidine, N-dodecyl-1,4,5,6-tetrahydropyrimidine, N-dodecyl-2-methyl-1,4,5,6-tetrahydropyrimidine, 2-n-heptadecyltetrahydropyrimidine, 1-(4-amino-4-propyl-5-pyrimidylmethyl)-2-methylpyridinium chloride hydrochloride, 2-(2'-furyl)benzimidazole (furidazole), 3-dodecyl-1-methyl-2-phenylbenzimidazolium ferricyanide, methyl-N-benzimidazol-2-yl-N-(butylcarbamoyl)carbamate (benomyl), 2-(ortho-chloroanilino) 4,6-dichloro-sym.-triazine, and 2-ethylamino-6-methyl-5-n-butyl-4-hydroxypyrimidine;

S-Heterocycles 5-chloro-4-phenyl-1,2-dithiol-3-one, 2,3-dicyano-1,4-dithia-anthraquinone (dithianone), and 2-(4-thiazolyl)benzimidazole;

NO-, NS- and OS-heterocycles 4-(2-chlorophenylhydrazono)-3-methyl-5-isoxazolone (drazoxolone), thiazolidinone-4-thione-(2) (rhodanine), 3-(parachlorophenyl)-5-methylrhodanine, 3,5-dimethyltetrahydro-1,3,5-thiadiazine-2-thione (dazomet), 3,3'-ethylene-bis(tetrahydro-4,6-dimethyl)-2H-1,3,5-thiadiazine-2-thione) (milneb), 3-benzylidene-amino-4-phenylthiazoline-2-thione, 6-chlorobenzthiazole-2-thiol zinc salt, 6-$\beta$-diethylaminoethoxy-2-dimethylamino-benzthiazole dihydrochloride, monoethanolammonium-benzthiazole-2-thiol, laurylpyridinium-5-chloro-2-mercaptobenzthiazole, zinc and sodium salts of 2-mercaptobenzthiazole and dimethyldithiocarbamate, 6-($\beta$-diethylaminoethoxy)-2-dimethylaminobenzthiazole dihydrochloride, 3-trichloromethylthiobenzothiazolone, 3-trichloromethylthiobenzoxazolone, 3-(trichloromethyl)-5-ethoxy-1,2,4-thiadiazole, 6-methyl-2-oxo-1,3-dithiolo[4,5-b]quinoxaline (quinomethionate), 2-thio-1,3-dithiolo[4,5-b]quinoxaline (thioquinox), 2,3-dihydro-5-carboxanilido-6-methyl-1,4-oxathine, 3,3,4,4-tetrachlorotetrahydrothiophene-1,1-dioxixide, and 2,3-dihydro-5-carboxanilido-6-methyl-1,4-oxanthine-4,4-dioxide;

Quaternary ammonium compounds

Cetyl-trimethylammonium bromide, n-alkyl($C_{12}$, $C_{14}$, $C_{16}$) dimethylbenzylammonium chloride, alkenyl-dimethylethylammonium bromide, dialkyldimethylammonium bromide, alkyldimethylbenzylammonium chloride, alkyl $C_9$-$C_{15}$tolylmethyltrimethylammonium chloride, di-isobutylcresoxyethyldimethylbenzylammonium chloride, para-di-isobutylphenoxyethoxyethyldimethylbenzylammonium chloride, and benzoyltrimethylammonium bromide;

Fungicidal antibiotics

Gliotoxin, 2,4-diguanidino-3,5,6-trihydroxycyclohexyl 5-deoxy-2-O-(2-deoxy-2-methylamino-$\alpha$-L-glucopyranosyl)3-C-formyl-$\beta$-L-hyxopentanofuranoside (streptomycin), 7-chloro-4,6-dimethoxycoumaran-3-one-2-spiro-1'-(2'-methoxy-6'-methylcyclohex-2'-en-4'-one) (griseofulvin), 4-dimethylamino-1,4,4$\alpha$,5,5$\alpha$,6,11,12$\alpha$-octahydro-3,5,6,10,12,12$\alpha$-hexahydroxy-6-methyl-1,11-dioxo-2-naphthacenecarboximide (oxytetracycline), 7-chloro-4-dimethylamino-1,4,4α,5,5α,6,11,12α-octahydro-3,6,10,12,12α-pentahydroxy-6-methyl-1,11-dioxo-2-naphthacenecarboximide (chlorotetracycline), (pimaricin), (lancomycin), (phleomycin), (kasugamycin), (phytoactin), D(-)-threo-2,2-dichloro-N-[β-hydroxy-α-(hydroxymethyl)-para-nitorphenethyl]aretamide (chloramphenicol), and blasticidine-S-benzylaminobenzene-sulphonate;

Miscellaneous substances

N-(3-nitrophenyl)itaconimide, phenoxyacetic acid, sodiumpara-dimethylaminobenzenediazosulphonate, acroleinephenylhydrazone, 2-chloroacetaldehyde(2,4-dinitrophenyl)-hydrazone, 2-chloro-3-(tolysulphonyl)-propionitrile, 1-chloro-2-phenylpentanediol(4,5)-thione(3), para-nonylphenoxypolyethyleneoxyethanol-iodine complex, (α-nitromethyl-ortho-chlorobenzylthioethylamine hydrochloride, 3-(paratert.-butylphenylsulphonyl)acrylonitrile, octachlorocyclohexanone, pentachlorobenzyl alcohol, pentachlorobenzyl acetate, pentachlorobenzaldehyde cyanohydrin, 2-norcamphanemethanol, 2,6-bis-(dimethylaminomethyl)-cyclohexanone, decachloro-octahydro-1,3,4-methano-2H-cyclobuta[ed]-pentalen-2-one, 1-(3-chloroallyl)-3,5,7-triaza-1-azoiaadamantane chloride, coal tar, and blast furnace tar;

Mixtures

Nickel sulphate/maneb mixture, maneb/mercaptobenzthiazole mixture, zineb/mercaptobenzthiazole mixture, zineb/nickel (II) chloride mixture, zineb/nickel(II) sulphate mixture, ziram/basic copper sulphate mixture, ziram/zinc/mercaptobenzthiazole mixture, thiram/cadmium hydrochloride mixture, thiram/hydroxymercury chlorophenol mixture, thiram/phenylmercury acetate mixture, polyethylene/bis-thiouram sulphide/copper oxychloride mixture, methylarsine/bis-(dimethyldithiocarbamate)/ziram/thiram mixture, folpet/phenylmercury acetate mixture, dodine/ferbam/-sulphur mixture, diethianone/copper oxychloride mixture, dichlone/ferbam/sulphur mixture, dinocap/dinitrooctylphenol mixture, captan/quintozene/tribasic copper sulphate mixture, cadmium propionate/-phenylmercury propionate mixture, formaldehyde/urea mixture and phenylammonium cadmium dilactate/phenylmercury formamide mixture.

The following examples illustrate but in no way limit the invention as hereinbefore described. Temperatures are given in degrees centigrade and parts by weight.

EXAMPLE 1 a. An amount of 230 g. of 2-bornylamine is dissolved in 1000 ml. of absolute toluene; into this solution at 30°–40° are fed 60 g. of dried hydrogen chloride gas, and into the obtained suspension at 100° are subsequently introduced 160 g. of dried phosgene within 5 hours. After cooling, the excess phosgene is removed by the passing through of a strong flow of air. The clear solution is concentrated in vacuo to dryness and the residue distilled. The 2-bornylisocyanate has the B.P.: 102°–104°, 12 Torr; and M.P.: 65°.

b. To a solution of 245 g. of 2-bornylisocyanate in 700 ml. of absolute tetrahydrofuran is added dropwise at 20°–30° a solution of 215 g. of 5-nonanone-oxime in 300 ml. of tetrahydrofuran. The clear solution is afterwards stirred for 5 hours at 40°; it is then allowed to cool before being concentrated in vacuo. The O-(bornyl(2)-carbamoyl)-5-nonanone-oxime has the B.P.: 95°–100° at 0.4 Torr. (Compound No 1)

The following compounds are prepared in a analogous manner.

| No. | Compounds | Physical data |
|---|---|---|
| 2 | O-(Dodecyl-carbamoyl)-2-butanone-oxime | B.P.: 127 – 136°/0,03 |
| 3 | O-(Dodecyl-carbamoyl)-4,4-dimethoxy-2-butanone-oxime | B.P.: 68 – 70° |
| 4 | O-(Bornyl(2)-carbamoyl)-4,4-dimethoxy-2-butanone-oxime | B.P.: 67 – 72°/0,03 |
| 5 | O-(1,4-Menthyl(3)-carbamoyl)-3-heptanone-oxime | B.P.: 62 – 64°/0,1 |
| 6 | O-(Bornyl(2)-carbamoyl)-2-nonanone-oxime | B.P.: 64 – 67°/0,1 |
| 7 | O-(1,4-Menthyl(3)-carbamoyl)-3-heptanone-oxime | B.P.: 69°/0,04 |
| 8 | O-(1,4-Menthyl(3)-carbamoyl)-2-methyl-7-ethyl-4-nonanone-oxime | B.P.: 82°/0,3 |
| 9 | O-(1,3,3-Trimethyl-norbonyl(2)-carbamoyl)-2-methyl-7-ethyl-4-nonanone-oxime | B.P.: 77 – 78°/0,04 |
| 10 | O-(Dodecyl-carbamoyl)-5-nonanone-oxime | B.P.: 170°/0,02 |
| 11 | O-(3,5,5-Trimethyl-cyclohexen(2)-yl-carbamoyl)-5-nonanone-oxime | B.P.: 72 – 78°/0,02 |
| 12 | O-(1,4-Menthyl(3)-carbamoyl)-5-nonanone-oxime | B.P.: 98 – 102 /0,02 |
| 13 | O-[Bicyclo[4.1.0]heptyl(7)-carbamoyl]-5-nonanone-oxime | B.P.: 79 – 82°/0,02 |
| 14 | O-(1,3,3-Trimethyl-norbornyl(2)-carbamoyl)-5-nonanone-oxime | B.P.: 74 – 76°/0,01 |
| 15 | O-(Dodecyl-carbamoyl)-benzaldehyde-oxime | M.P.: 67 – 69° |
| 16 | O-(Dodecyl-carbamoyl)-4-chlorobenzaldehyde-oxime | M.P.: 58 – 60° |
| 17 | O-(Cyclohexyl-carbamoyl)-benzaldehyde-oxime | M.P.: 128 – 130° |
| 18 | O-(Cyclohexyl-carbamoyl)-4-chlorobenzaldehyde-oxime | M.P.: 134 – 137° |
| 19 | O-(Bornyl(2)-carbamoyl)-4-chlorobenzaldehyde-oxime | M.P.: 132 – 134° |
| 20 | O-(Dodecyl-carbamoyl)-acetophenone-oxime | M.P.: 59 – 61° |
| 21 | O-(Cyclohexyl-carbamoyl)-acetophenone-oxime | $n_D^{40}$ = 1.5495 |
| 22 | O-(1,3,3-Trimethyl-norbornyl(2)-carbamoyl)-aceto-phenone-oxime | B.P.: 78 – 81°/0,02 |
| 23 | O-(Dodecyl-carbamoyl)-propio-phenone-oxime | M.P.: 68 – 70° |
| 24 | O-(Bornyl(2)-carbamoyl)-propiophenone-oxime | nondistillable oil |
| 25 | O-(1,4-Menthyl(3)-carbamoyl)-4-phenyl-2-butanone-oxime | B.P.: 101 – 105°/0.6 |
| 26 | O-(1,3,3-Trimethyl-norbornyl(2)-carbamoyl)-4-phenyl-2-butanone-oxime | M.P.: 115 – 117° |
| 27 | O-(Bornyl(2)-carbamoyl)-4-phenyl-2-butanone-oxime | B.P.: 110 – 112°/0.7 |
| 28 | O-(Dodecyl-carbamoyl)-cyclopentanone-oxime | M.P.: 48 – 50° |
| 29 | O-(Cyclohexyl-carbamoyl)-cyclopentanone-oxime | M.P.: 49 – 50° |
| 30 | O-(3,5,5-Trimethyl-cyclohexen(2)-yl-carbamoyl)-cyclopentanone-oxime | M.P.: 111 – 113° |
| 31 | O-(1,4-Menthyl(3)-carbamoyl)-cyclopentanone-oxime | M.P.: 97 – 100° |
| 32 | O-(Bornyl(2)-carbamoyl)-cyclopentanone-oxime | M.P.: 60 – 62° |
| 33 | O-(3,5,5-Trimethyl-cyclohexen(2)-yl-carbamoyl)-cyclohexanone-oxime | M.P.: 58 – 62° |
| 34 | O-(1,4-Menthyl(3)-carbamoyl)-cyclohexanone-oxime | M.P.: 83 – 85° |
| 35 | O-(1,3,3-Trimethyl-norbornyl(2)-carbamoyl)-cyclohexanone-oxime | M.P.: 112 – 114° |
| 36 | O-(Bornyl(2)-carbamoyl)-cyclohexanone-oxime | $n_D^{40}$ = 1.5103 |
| 37 | O-(3,5,5-Trimethyl-cyclohexen(2)-yl-carbamoyl)-cycloheptanone-oxime | B.P.: 72 – 73°/0.02 |
| 38 | O-(1,4-Menthyl(3)-carbamoyl)-cycloheptanone-oxime | B.P.: 120°/0.02 |
| 39 | O-(1,3,3-Trimethyl-norbornyl(2)-carbamoyl)-cycloheptanone-oxime | M.P.: 85 – 87° |

| No. | Compounds | Physical data |
|-----|-----------|---------------|
| 40 | O-[Bicyclo[4.1.0]heptyl(7)-carbamoyl]-cycloheptanone-oxime | M.P.: 70 – 72° |
| 41 | O-(Bornyl(2)-carbamoyl)-cycloheptanone-oxime | $n_D^{40} = 1.5092$ |
| 42 | O-(Dodecyl-carbamoyl)-cyclododecanone-oxime | $n_D^{40} = 1.4830$ |
| 43 | O-(1,3,3-Trimethyl-norbornyl(2)-carbamoyl)-cyclododecanone-oxime | M.P.: 133 – 135° |
| 44 | O-(1,4-Menthyl(3)-carbamoyl)-1,4-menthone(3)-oxime | B.P.: 87 – 89°/0,2 |
| 45 | O-(1,3,3-Trimethyl-norbornyl(2)-carbamoyl)-1,4-menthone(3)-oxime | B.P.: 94 – 96°/0,09 |
| 46 | O-(Bornyl(2)-carbamoyl)-1,4-menthone(3)-oxime | B.P.: 130 – 135°/0,5 |
| 47 | O-(1,4-Menthyl(3)-carbamoyl)-2-bornanone-oxime | $n_D^{20} = 1.4984$ |
| 48 | O-(1,3,3-Trimethyl-norbornyl(2)-carbamoyl)-2-bornanone-oxime | M.P.: 152 – 155° |
| 49 | O-(Bornyl(2)-carbamoyl)-bornanone(2)-oxime | M.P.: 181 – 184° |
| 50 | O-(1,3,3-Trimethyl-norbornyl(2)-carbamoyl)-tricyclo[2.2.1.0$^{2.6}$]-3-heptanone-oxime | B.P.: 126 – 130°/0,2 |
| 51 | O-(Bornyl(2)-carbamoyl)-tricyclo[2.2.1.0$^{2.6}$]-3-heptanone-oxime | $n_D^{40} = 1.5193$ |
| 52 | O-(Octyl-carbamoyl)-bornanone (2)-oxime | $n_D^{26} = 1.4895$ |
| 53 | O-(Decyl-carbamoyl)-bornanone (2)-oxime | $n_D^{26} = 1.4867$ |
| 54 | O-(Dodecyl-carbamoyl)-bornanone (2)-oxime | $n_D^{26} = 1.4861$ |
| 55 | O-(Tetradecyl-carbamoyl)-bornanone (2)-oxime | M.P. 52 – 54° |
| 56 | O-(Cyclohexyl-carbamoyl)-bornanone (2)-oxime | $n_D^{30} = 1.5092$ |
| 57 | O-(Cyclooctyl-carbamoyl)-bornanone (2)-oxime | $n_D^{26} = 1.5119$ |
| 58 | O-(Benzyl-carbamoyl)-bornanone (2)-oxime | M.P. 75 – 79° |
| 59 | O-(1,4-Menthyl (3)-carbamoyl)-tricyclo[2.2.1.0$^{2.6}$]-3-heptanone-oxime | M.P. 131 – 132° |

EXAMPLE 2

A. Dusting agents

For the preparation of (a) a 10% dust, (b) a 5% dust, and (c) a 2% dust, the following materials are used:

a.

10 parts of 0-(3,5,5-trimethylcyclohexen(2)-yl-carbamoyl)-5-nonanone-oxime, (No. 11)
5 parts of highly dispersed silicic acid,
85 parts of talcum;

b.

5 parts of 0-(3,5,5-trimethylcyclohexen(2)-yl-carbamoyl)-cycloheptanone-oxime, (No. 37)
95 parts of talcum;

c.

2 parts of 0-(bornyl(2)-carbamoyl)-5-nonanone-oxime,
1 part of highly dispersed silicic acid, (No. 1)
97 parts of talcum.

The above listed active substances are intimately mixed and ground with the carriers. The thus obtained fungicidal dusting agents are used for the treatment of the soil of seed beds, or for the dusting of plants.

B. Wettable powders

The following constituents are used for the preparation of (a) a 50%, (b) a 40%, (c) a 25%, and (d) a 10% wettable powder:

a.

50 parts of 0-(bicyclo[4.1.0]heptyl-carbamoyl)-cycloheptanone-oxime, (No. 40)
5 parts of naphthalenesulphonic acid-benzenesulphonic acid formaldehyde condensate,
5 parts of dibutylnaphthalenesulphonic acid,
5 parts of Champagne chalk,
20 parts of silicic acid,
15 parts of kaolin;

b.

40 parts of 0-(cyclohexyl-carbamoyl)-acetophenone-oxime,(No.21)
1 part of dibutylnaphthalenesulphonic acid,
5 parts of ligninsulphonic acid-sodium salt,
2 parts of 1:1 mixture of Champagne chalk and hydroxyethyl cellulose,
30 parts of kaolin,
22 parts of sodium-aluminum-silicate;

c.

25 parts of 0-(bornyl(2)-carbamoyl)-5-nonanone-oxime,(No. 1)
5 parts of oleyl methyl tauride sodium salt,
2.5 parts of naphthalenesulphonic acid-formaldehyde-condensate,
0.5 parts of carboxymethyl cellulose,
5 parts of neutral potassium aluminium silicate,
62 parts of talcum;

d.

10 parts of O-(3,5,5-trimethylcyclohexen(2)-yl-carbamoyl)-cycloheptanone-oxime, (No. 37)
3 parts of a mixture of the sodium salt of saturated fatty alcohol sulphates,
5 parts of naphthalenesulphonic acid-formaldehyde-condensate,
82 parts of kaolin.

The active substances are intimately mixed, in suitable mixers, with the additives, and then ground on suitable grinding mills and rollers. Wettable powders are thus obtained which can be diluted with water to form suspensions of any desired concentration. Such suspensions are used mainly for the protection of plants.

C. Paste

The following materials are used for the preparation of a 45% paste:

45 parts of O-(cyclohexyl-carbamoyl)-acetophenone-oxime, (No. 21)
5 parts of sodium aluminum silicate,
14 parts of cetyl polyglycol ether with 8 moles of ethylene oxide,
1 part of oleyl polyglycol ether with 5 moles of ethylene oxide,
2 parts of spindle oil,
10 parts of polyethylene glycol,
23 parts of water.

The active substance is intimately mixed and ground, in suitable equipment, with the additives. A paste is obtained, from which can be produced, by dilution with water, suspensions of any desired concentration. These suspensions are mainly used for plant protection.

D. Emulsion

9–1 = linear decrease in infection;
0 = no infection.

| No. | Compound | |
|---|---|---|
| 31 | O-(1,4-Menthyl(3)-carbamoyl)-cyclopentanone-oxime | 3 |
| 30 | O-(3,5,5-Trimethyl-cyclohexen(2)-yl-carbamoyl)-cyclopentanone-oxime | 1 |
| 37 | O-(3,5,5-Trimethyl-cyclohexen(2)-yl-carbamoyl)-cycloheptanone-oxime | 2 |
| 2 | O-(Dodecyl-carbamoyl)-2-butanone-oxime | 0 |
| 3 | O-(Dodecyl-carbamoyl)-4,4-dimethoxy-2-butanone-oxime | 3 |
| 42 | O-(Dodecyl-carbamoyl)-cyclododecanone-oxime | 1 |
| 20 | O-(Dodecyl-carbamoyl)-acetophenone-oxime | 0 |
| 4 | O-(Bornyl(2)-carbamoyl)-4,4-dimethoxy-2-butanone-oxime | 4 |
| 32 | O-(Bornyl(2)-carbamoyl)-cyclopentanone-oxime | 0 |
| 36 | O-(Bornyl(2)-carbamoyl)-cyclohexanone-oxime | 0 |
| 41 | )-(Bornyl(2)-carbamoyl)-cycloheptanone-oxime | 2 |
| 35 | O-(1,3,3-Trimethyl-norbornyl(2)-carbamoyl)-cyclohexanone-oxime | 3 |
| 39 | O-(1,3,3-Trimethyl-norbornyl(2)-carbamoyl)-cycloheptanone-oxime | 3 |
| 17 | O-(Cyclohexyl-carbamoyl)-benzaldehyde-oxime | 3 |
| | O-(Octahydro-1,2,4-methenopentalenyl(5)-carbamoyl)-propiophenone* | 10 |
| | O-(Octahydro-1,2,4-methenopentalenyl(5)-carbamoyl)-5-nonanone-oxime* | 8 |

*known from the French Patent Specification No. 1,549,790

The following ingredients are mixed together for the preparation of a 10% emulsion concentrate:
10 parts of O-(1,4-methyl-(3)-carbamoyl)-cyclopentanone-oxime, (No. 31)
55 parts of xylene,
32 parts of dimethylformamide,
3 parts of composite emulsifier (nonylphenolpolyoxyethylene- and dodecylbenzene-Ca-sulphonate).

This concentrate can be diluted with water to obtain emulsion of a concentration suitable for plant protection.

EXAMPLE 3

Action against Botrytis cinerea on *Vicia faba* (broad beans)

Petri dishes were lined with moist filter paper and into each dish were then placed three well developed and uniformly large leaves of Vicia faba; the leaves were subsequently sprayed until dripping wet with a liquor prepared from the active substance in the form of wettable powder (0.1% active substance content). After the leaves had again become dry they were infected with a freshly prepared fungi spore suspension and kept for 1–2 days in a moist atmosphere at 18°–20°C. After this time there firstly appeared on the leaves small black specks which rapidly spread. The number and magnitude of the areas of infection serve as a criterion for the assessment of the effectiveness of the test substance.

The interpretation of the numbers used in the following table is given below:
10 = ineffective, infection equally as severe as in the case of the untreated control plants;
9–1 = linear decrease in degree of infection;
0 = no infection.

EXAMPLE 4

Action on *Erysiphe cichoracearum* (powdery mildew of cucumbers) on cucumbers (*Cucumis sativus*)

Young cucumber plants were sprayed dripping wet with a 1% suspension of the active substances formulated as wettable powder. When the plants were again dry they were infected with a spore suspension of powdery mildew of cucumbers, and subsequently placed in a green-house at ca. 23°. After 8 days the degree of infection (proportion of leaf-surface covered by fungal coating) on the infected treated leaves compared with that on infected untreated control specimens is determined.

The interpretation of the numbers appearing in the following table is given below:
10 = ineffective, infection equally as severe as that obtained on the untreated control plants;
9–1 = linear descrease in degree of infection;
0 = no infection.

| No. | Compound | |
|---|---|---|
| 1 | O-(Bornyl(2)-carbamoyl)-5-nonanone-oxime | 0 |
| 17 | O-(Cyclohexyl-carbamoyl)-benzaldehyde-oxime | 4 |
| 11 | O-(3,5,5-Trimethyl-cyclohexen(2)-yl-carbamoyl)-5-nonanone-oxime | 2 |
| 30 | O-(3,5,5-Trimethyl-cyclohexen(2)-yl-carbamoyl)-cyclopentanone-oxime | 4 |
| 13 | O-(Bicyclo[4.1.0]heptyl-carbamoyl)-5-nonanone-oxime | 1 |
| 40 | O-(Bicyclo[4.1.0]heptyl-carbamoyl)-cycloheptanone-oxime | 3 |
| | O-(Oktahydro-1,2,4-methenopentalenyl(5)-carbamoyl)-pentanone-oxime* | 10 |

*known from the French Patent Specification No. 1,549,790

EXAMPLE 5

Action against *Phytophthora infestans* (blight on leaves and tubers) on tomatoes (*solanum lycopersicum*)

Tomatoes of the same type and in an identical stage of development were sprayed with a liquor of 0.1% of active substance (prepared from the active substance processed into the form of a wettable powder). When the tomatoes were again dry they were infected with a spore suspension of *Phytophthora infestans* and kept for about 6 days in a green-house at 18°–20° with a high level of atmospheric moisture (95–100%). After this period they exhibit typical leaf spots. An assessment of the tested substances was made on the basis of the number and size of the leaf spots.

The interpretation of the number appearing in the following table is given below:

10 = ineffective, infection equal to that on the untreated control plants;
9–1 = linear decrease in degree of infection;
0 = no infection.

| No. | Compound | |
|---|---|---|
| 49 | O-(Bornyl(2)-carbamoyl)-2-bornanone-oxime | 4 |
| 21 | O-(Cyclohexyl-carbamoyl)-acetophenone-oxime | 4 |
| 5 | O-(1,4-Menthyl(3)-carbamoyl)-2-nonanone-oxime | 4 |
| 44 | O-(1,4-Menthyl(3)-carbamoyl)-1,4-menthon-(3)-oxime | 4 |

EXAMPLE 6

Action on *Uromyces appendiculates* (bean rust) on beans (*Phaseolus vulgaris*)

Bean plants in the two-leaf stage were sprayed until dripping wet with a suspension of the active substances made up as wettable powder (conc. 0.1% of active substance). When the plants were again dry they were infected with a freshly prepared bean rust spore suspension (5 plants per product), and kept for 1 day in a moist chamber and then in a green-house at 20°–22°. Evaluation of the test results is based on the number of rust spots present after about 8–12 days.

The numbers in the following table have the meanings given below:

10 = ineffective, infection equally as severe as that on the untreated control plants;
9–1 = linear decrease in degree of infection;
0 = no infection.

EXAMPLE 7

Action against Potato Virus-Y on pepper (*Capsicum annuum*)

Two separate groups of 15 pepper plants were sprayed 3 days after unfolding of the seedling leaves, with solutions containing 1000 and 2000 ppm of active substance respectively in the form of a aqueous suspension. 24 hours after this treatment each plant was mechanically inoculated. The evaluation of the results was carried out 1 week later and may be sumarized as follows:

| No. | Compound | conc. (ppm) | value |
|---|---|---|---|
| 18 | O-(Cyclohexyl-carbamoyl)-4-chloro-benzaldehyde-oxime | 1000 | 3 |
|  |  | 2000 | 2 |
| 33 | O-(3,3,5-Trimethyl-cyclohexen(5)-yl-carbamoyl)-cyclohexanone-oxime | 1000 | 7 |
|  |  | 2000 | 2 |
| 34 | O-(1,4-Menthyl(3)-carbamoyl)-cyclohexanone-oxime | 1000 | 9 |
|  |  | 2000 | 1 |
| 47 | O-(1,4-Menthyl(3)-carbamoyl)-bornanone(2)-oxime | 1000 | 4 |
|  |  | 2000 | 2 |
| 48 | O-(1,3,3-Trimethyl-norbornyl(2)-carbamoyl)-bornanone(2)-oxime | 1000 | 4 |
|  |  | 2000 | 2 |
| 49 | O-(Bornyl(2)-carbamoyl)-bornanone-(2)-oxime | 1000 | 4 |
|  |  | 2000 | 4 |

10 = ineffective, infection equally severe as that on untreated control plants;
9–1 = linear decrease in degree of infection;
0 = no infection.

What we claim is:
1. O-(1,4-Menthyl(3)-carbamoyl)-cyclopentanone oxime.
2. O-(1,4-Menthyl(3)-carbamoyl)-2-bornanone oxime.
3. O-(3,5,5-Trimethyl-cyclohexene(2)-yl-carbamoyl)-5-nonanone oxime.
4. O-(bicyclo[4.1.0]heptyl-carbamoyl)-cycloheptanone oxime.
5. O-(1,3,3-Trimethyl-norbornyl(2)-carbamoyl)-5-nonanone oxime.
6. O-(Bornyl(2)-carbamoyl)-5-nonanone oxime.

* * * * *

| No. | Compound | |
|---|---|---|
| 11 | O-(3,5,5-Trimethyl-cyclohexen(2)-yl-carbamoyl)-5-nonanone-oxime | 4 |
| 40 | O-(Bicyclo[4.1.0]heptyl-carbamoyl)-cycloheptanone-oxime | 0 |
| 17 | O-(Cyclohexyl-carbamoyl)-benzaldehyde-oxime | 0 |
| 18 | O-(Cyclohexyl-carbamoyl)-4-chlor-benzaldehyde-oxime | 1 |
|  | O-(Octahydro-1,2,4-methenopentalenyl(5)-carbamoyl)-propiophenone-oxime* | 10 |
|  | O-(Octahydro-1,2,4-methenopentalenyl(5)-carbamoyl)-cyclohexanone-oxime* | 10 |

*known from the French Patent Specification No. 1,549,790